United States Patent [19]

Shaw

[11] Patent Number: 4,938,769
[45] Date of Patent: Jul. 3, 1990

[54] MODULAR TIBIAL PROSTHESIS

[76] Inventor: James A. Shaw, 1424 Woodhaven Dr., Hummelstown, Pa. 17036

[21] Appl. No.: 359,389

[22] Filed: May 31, 1989

[51] Int. Cl.$^5$ .............................................. A61F 2/38
[52] U.S. Cl. ...................................................... 623/20
[58] Field of Search ...................... 623/16, 18, 19, 20, 623/22, 23

[56] References Cited

U.S. PATENT DOCUMENTS

| | | | |
|---|---|---|---|
| 3,605,123 | 9/1971 | Hahn | 623/18 |
| 3,855,638 | 12/1974 | Pilliar | 623/18 |
| 4,257,129 | 3/1981 | Volz | 623/20 |
| 4,309,778 | 1/1982 | Buechel et al. | 623/20 |
| 4,340,978 | 7/1982 | Buechel et al. | 623/20 |
| 4,358,859 | 11/1982 | Schurman et al. | 623/20 |
| 4,462,120 | 7/1984 | Rambert et al. | 623/20 |
| 4,470,158 | 9/1984 | Pappas et al. | 623/20 |
| 4,479,271 | 10/1984 | Bolesky et al. | 623/20 |
| 4,550,448 | 11/1985 | Kenna | 623/20 |
| 4,551,863 | 11/1985 | Murray | 623/20 |
| 4,759,767 | 7/1988 | Lacey | 423/20 |

FOREIGN PATENT DOCUMENTS 2184025 6/1987 United Kingdom .................. 623/20

OTHER PUBLICATIONS

"Discover," Oct. 1987, pp. 22–23.
"Scientific American," Jan. 1978, pp. 44–51.
"Proc. Advances in Bioengineering Symposium," Dec. 1978, ASME, New York, NY, 1978, pp. 49–53.
"Clin. Orthop.," Jan.–Feb. 1985, pp. 34–39.
"J. Arthroplasty," vol. 1, 1986, pp. 293–296.
"J. Biomed. Mat. Res.," vol. 7, 1973, pp. 301–311.
"J. Arthroplasty," Oct. 1988 Supplement, pp. S87–S94.
"Orthopedics," vol. 12, Jan. 1989, pp. 10–11.
Kirschner, "Truly Modular T", Kirschner Medical Corp. Brochure-1-1989.

*Primary Examiner*—David J. Isabella
*Attorney, Agent, or Firm*—Richard L. Hansen

[57] ABSTRACT

This invention provides a tibial prosthesis for use during a total knee arthroplasty procedure which includes a modular tibial component comprising an in-bone anchorage assembly to which is removably attached a tibial tray adapted to receive and retain a variety of femoral components or bearing inserts. Removal of the tray permits access to the interface between the bone and anchorage assembly in the event removal or revision are necessary. In preferred embodiments, the invention affords hybrid fixation of the tibial prosthesis in that bone cement for immediate fixation and adaptation for longer term bone ingrowth are featured.

22 Claims, 4 Drawing Sheets

MODULAR TIBIAL PROSTHESIS

This invention is in the field of prosthetic replacements for human joints. More specifically, the invention is directed to artificial knee joints, especially to the tibial component of such prostheses.

BACKGROUND OF THE INVENTION

The knee is one of the most complex joints in the human body. Anatomically, the knee provides articulation between the femur and the tibia. The medial and lateral femoral condyles are in contact with complementary cartilaginous menisci on the proximal end of the tibia. The relative motions of the femur and tibia about these surfaces of contact are modulated by five ligaments and three muscle groups. The femur and tibia are united by pairs of cruciate and collateral ligaments as well as the patellar ligament. The muscles comprise the hamstring, gastrocnemius and quadriceps groups. Relative motion between the femur and tibia is an intricate synergy of hinge-like flexion and extension, anteroposterior translation (roll-back) and axial rotation.

In normal activities, such as walking and jogging, kneeling, climbing stairs, and getting into or out of chairs, peak loads equal to about five times the weight of the body are applied to the knee joint. Much higher stresses are put on the joint during participation in sports such as tennis, soccer, football, and distance running.

Thus, it is not surprising that knee injuries occur frequently, especially to the menisci and ligamentous supporting structures. Such injuries may lead to chronic swelling and inflammation and eventually to arthritic deterioration. Additionally, arthritic joint destruction may occur as a natural sequelae of cartilage cell senescence or as a result of multiple inflammatory disease processes.

As an arthritic knee may be painful and functionally debilitating, a need exists for prosthetic components to replace the natural joint surfaces which have been damaged by the arthritic process. It has been estimated that approximately 40,000 Americans undergo prosthetic knee replacement procedures per year as a result of arthritic deterioration (*Discover*, October 1987, pp. 22-23).

The first total knee prosthesis was successfully introduced by Borje Walldius in the early 1950's. The Walldius prosthesis is an example of an "articulated" or "constrained" prosthesis in that the femoral and tibial components are mechanically linked, the muscle/ligament structures of the natural knee not being relied upon to hold the femur and tibia together.

Unconstrained total knee prostheses were introduced in 1971 by Frank Gunston, as represented by the Polycentric prosthesis. The Gunston prosthesis, like many subsequent designs, had femoral and tibial components that were "nonarticulated". In other words, the femoral and tibial components were not connected mechanically, the patient's muscles and ligaments being relied on to hold the knee together in a physiological fashion. More recent unconstrained prosthesis designs feature nearly anatomically shaped components, and are commonly referred to as "anatomical" or "surface replacement" or "cruciate ligament retaining" prostheses. Still other designs impart varying degrees of intrinsic support to the knee joint to compensate for lost ligament support and are termed "semi-constrained" prostheses. Descriptive terms such as "cruciate ligament substituting" or "posteriorly constrained" or "stabilized" are frequently used.

In 1978 it was estimated that more than 80 different prosthetic knees were available (*Scientific American*, January 1978, pp. 44-51), and there has been intense activity in the areas of prosthesis design since that time. More recent developments in constrained (articulated) total knee prostheses are represented in U.S. Pat. No. 4,358,859 and in U.S. Pat. No. 4,462,120, the latter of which describes femoral and tibial components in which the bearing members may be detached for replacement when worn. U.S. Pat. Nos. 4,309,778; 4,340,978; and 4,470,158 exemplify knee prostheses of the unconstrained type, and U.S. Pat. No. 4,257,129 describes a tibial component featuring a replaceable articulation member.

Currently available knee prostheses typically rely on either poly(methylmethacrylate) bone cement or natural bone ingrowth for fixation. For example, U.S. Pat. No. 4,479,271 describes a tibial component for a knee prosthesis in which a layer of fibrous metal mesh is incorporated to encourage bone ingrowth. Other types of porous-coat surface treatments, designed to encourage natural bone ingrowth, are disclosed in U.S. Pat. Nos. 3,605,123; 3,855,638; and 4,550,448; for example. U.S. Pat. No. 4,551,863 describes fixation using bone cement in combination with bone ingrowth, most specifically as applied to a hip prosthesis.

Failure of fixation of prosthetic components is one of the most frequent mechanical complications associated with total knee arthroplasty (see *Proc. Advances in Bioengineering Symposium*, December 1978, Published by ASME, New York, N.Y., 1978, pp 49-53 and *Clin. Orthop.*, January-February 1985, pp 34-39, for example). When bone cement fixation is employed, failure often occurs at the bone/cement interface (*J. Arthroplasty*, vol. 1, 1986, pp 293-296).

Whereas it might be expected that natural bone ingrowth would improve the integrity of the bond between prosthesis and bone and thereby ameliorate the problem, such bony ingrowth is by no means readily achieved, even with the most advanced porous-coated prosthesis surfaces. Apparently, bony ingrowth will not occur readily if there is even slight relative motion between the bone and the adjacent ingrowth surface (see *J. Biomed. Mat. Res.*, vol. 7, 1973, pp 301-311, for example).

Another serious outstanding problem in knee replacement surgery relates to the technical difficulty of removing the prosthetic component. Prosthetic component removal may prove necessary under several circumstances including: structural failure or loosening of one or more components, articulating surface wear, ligamentous instability problems, bony fracture or resorption, or joint infection.

Of particular concern is the removal of the tibial component, in that access to the intramedullary stem, which is commonly employed to improve component fixation and stability, may be prohibitively difficult. Complications associated with tibial component removal include gross bone loss and tibial fracture, as well as extended operating time and creation of particulate metal and plastic debris (*J. Arthroplasty*, October 1988 Supplement, pp. 587-594).

Various attempts have been made to solve this problem. For example, certain tibial components incorporate slots surrounding the intramedullary fixation stem through which osteotomes may be inserted to break any existing bond to the prosthetic component. Unfortunately, inclusion of slots may compromise the structural integrity of the component and create a predisposition to fatigue failure. Other tibial component designs simply avoid the problem by eliminating intramedullary stems or employing stems of smooth contour so that they may be extracted from bone or a surrounding cement mantel with comparative ease. This option lessens extraction difficulty, but may compromise fixation and long term stability.

It is to the aforecited problems that the present invention is directed. Consequently, it is one object of this invention to provide a tibial prosthesis which facilitates fixation. It is a further objective to provide a tibial component which is readily manipulated to provide clear access to the anchoring mechanism in the event the tibial prosthesis must be revised or removed. It is yet a further objective to provide a modular tibial component which can be employed with a selection of femoral or bearing insert components. Other objectives and advantages of the invention will become apparent hereinafter.

SUMMARY OF THE INVENTION

These objectives are attained in the hybrid fixation modular tibial prosthesis which constitutes one aspect of this invention; other aspects include portions of the prosthesis. The tibial prosthesis is intended to be used as part of a total knee prosthesis and is adapted to be compatible with other components thereof, such as femoral and patellar prostheses. The adaptation is effected in part, for example, by equipping the tibial prosthesis with an interchangeable, modular bearing insert that mates with the femoral portion of a total knee prosthesis. Such bearing inserts are well known in the art and, typically, are fabricated from a synthetic polymer, such as polyethylene.

In another aspect, this invention comprises a modular tibial component which is part of the prosthesis and includes a tibial tray adapted to receive and retain the interchangeable, modular bearing insert referred to above, or alternatively, a femoral component. The tibial tray is also adapted to removably attach to an in-bone anchorage assembly. Trays of various sizes are interchangeable, advantageously reducing required inventories. In preferred embodiments, the tibial component is adapted to achieve immediate fixation via an appropriate adherent, and longer term stability via bone ingrowth.

In yet another aspect, the invention comprises the inbone anchorage assembly per se, the anchorage assembly being adapted to permit removal and replacement, if necessary, of the tibial tray, thereby facilitating access to the interface between the anchorage assembly and the bone in the event revision or removal of the prosthesis becomes necessary.

In other aspects this invention provides methods for restoring an injured knee utilizing the articles referred to above.

The invention in its various aspects will be understood more readily by reference to the drawings which accompany this specification and the detailed description which follows.

DETAILED DESCRIPTION OF THE INVENTION

Figure 1:
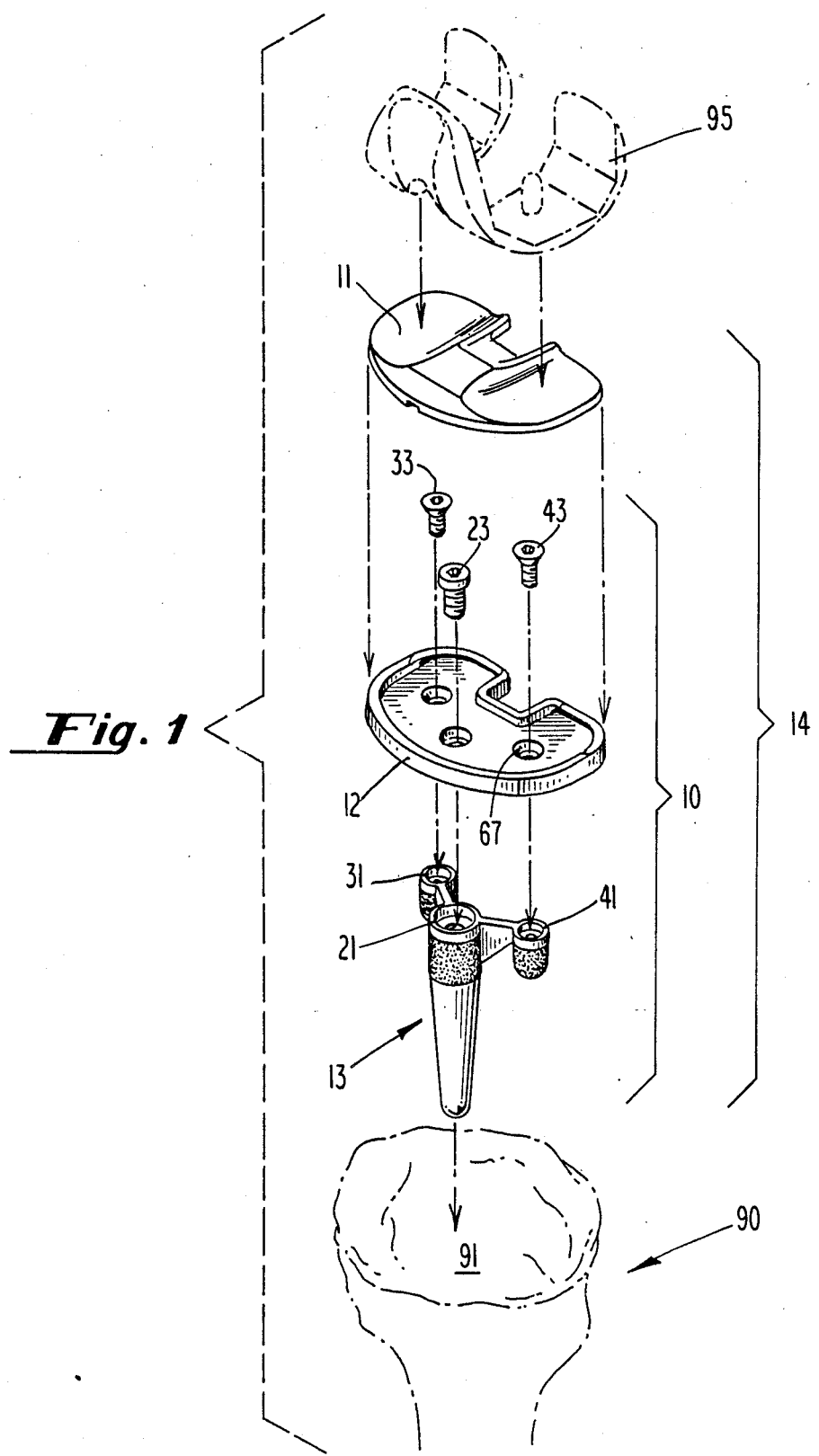
FIG. 1 is an exploded view, in perspective, of a preferred embodiment of the tibial prosthesis of this invention in relation to other components with which it is used.
Figure 2:
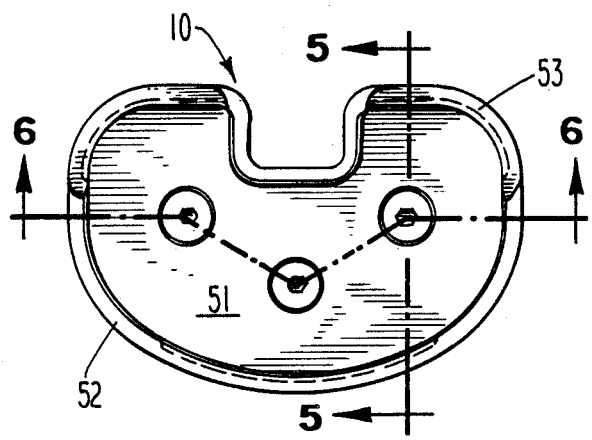
FIG. 2 is a plan view of a preferred embodiment of the modular tibial component of this invention.

With reference first to FIG. 1, a tibial prosthesis 14 of this invention includes modular tibial component 10 and bearing insert 11. The bearing insert is adapted to mate with femoral component 95 of a total knee prosthesis. The modular tibial component 10, in turn, includes tibial tray 12, in-bone anchorage assembly 13, and fasteners 23, 33, and 43. Tibial tray 12 is thus adapted to removably attach to in-bone anchorage assembly 13 and is also adapted to receive and retain bearing insert 11. Anchorage assembly 13 is structured to be implanted in surgically prepared proximal end 91 of tibia 90.

In-bone anchorage assembly 13 includes central stem 20 having a proximal terminus 21 and a distal terminus 22. The stem is elongated along its axis 28 and is structured to fit within the intramedullary canal (not shown) of tibia 90. The anchorage assembly includes, as well, a pair of elongated fixation pegs 30 and 40 spaced symmetrically from the central stem 20 to enter the posterior-lateral and posterior-medial quadrants of the tibia. Fins 81 and 82 structurally connect fixation pegs 30 and 40, respectively, with central stem 20. Proximal termini 31 and 41 of fixation pegs 30 and 40, respectively, together with stem terminus 21, which are in triangular relationship, define an attachment table 80. Means, e.g., fasteners 23, 33 and 43, are provided for removably attaching tibial tray 12 to the anchorage assembly in the attachment table as described more fully below.

Although the illustrated embodiment includes two fixation pegs, 30 and 40, additional fixation pegs optionally may be provided; it is only necessary that the anchorage assembly include a plurality of fixation pegs. Fixation pegs 30 and 40 provide specific support beneath the highest load-bearing portions of bearing insert 11, increase the surface area for fixation, and stabilize the prosthesis against torsional forces.

In general, it is preferred that central stem 20 and fixation pegs 30 and 40 be axially elongated substantially in parallel. Furthermore, although the preferred embodiment depicts axis 28 of central stem 20 to be perpendicular to attachment table 80 in all planes, an angular relationship may be incorporated to simulate the naturally occurring posterior slope of the tibial articular surface and/or the naturally occurring varus alignment of the tibial articular surface with respect to the long axis of the tibia. This angular relationship would not exceed 5 to 10 degrees under most circumstances. Central stem 20, as well as the fixation pegs, should be sized to fit within the available tibial bone stock.

Central stem 20 preferably is tapered toward distal terminus 22 and is adapted for intramedullary press fit in the tibia. Although not required, it is further preferred that both central stem 20 and fixation pegs 30 and 40 be substantially cylindrical in cross-sections perpendicular to their elongation axes 28, 38 and 48.

At least a portion of the exposed surface of the in-bone anchorage assembly preferably is specially adapted to enhance fixation to the tibia. Such adaptation may be aimed at enhancing fixation by means of adhesive resins, bone cements, or live bone ingrowth, for example. Live bone ingrowth can be enhanced by methods known in the art, such as including a porous metal or ceramic surface preparation or a hydroxyapatite or tricalcium phosphate coating. Preferably, at least part of the surface of central stem 20 is specially adapted to enhance fixation; most preferably, at least part of the proximal one-half of the surface.

Although other bio-compatible materials can be employed, the use of a metallic in-bone anchorage assembly is favored, e.g., medical grade titanium or a chromium-cobalt alloy. When such metal is employed, it is preferred that fixation of the assembly be enhanced by means of a porous metal coating 83 applied to, for example, pegs 30 and 40, as well as central stem 20. Suitable porous metal coatings are described in references cited above, including U.S. Pat. No. 4,550,448. In the event that a porous coating is employed to enhance fixation, it is especially advantageous to construct the assembly in such a way that at least a part of the coating is protuberant, i.e., is raised above the surrounding uncoated surface as protuberant area 84 on central stem 20, to enhance contact between the bone and porous surface.

Fins 81 and 82, which act as structural links connecting the fixation pegs to the central stem and resist torsional forces acting on the prosthesis, can be replaced by equivalent structures having a different form. Preferably, fins 81 and 82 are elongated distally toward central stem 20 for press fit in the tibia and terminate proximally in attachment table 80. Most preferably, the fins also taper distally from table 80 to assist tibial insertion.

The in-bone anchorage assembly 13 includes means for removably attaching a tibial tray, such as tibial tray 12, for example, to the anchorage assembly. Although various techniques can be employed, e.g., Morse tapers, it is convenient to adapt the proximal termini 21, 31 and 41 to receive fasteners for removably attaching the tibial tray along attachment table 80. Such fasteners may be threaded fasteners, such as assembly screws 23, 33 and 43, for example, the proximal termini being drilled and tapped to receive the threaded fasteners. When such assembly screws are employed, taps and screws having "Spiralock" threads are preferred ("Spiralock" is a trademark of H. O. Holmes, licensed to Detroit Tool Industries).

Tibial tray 12, sized and flattened to fit the prepared tibia, has a proximal side 51 which is adapted to receive and retain bearing insert 11 as further described hereinafter. As shown in FIGS. 1-6, the tibial tray is notched posteriorly to clear the cruciate ligaments, but this is not a requisite feature, e.g., see FIG. 7. The tibial tray also has a distal side 55, most completely shown in FIGS. 4-6. Although not required, it is preferred that distal side 55 carry a narrow, axially raised flange 56 about its periphery. When the tray is properly positioned with respect to the prepared tibia, flange 56 acts as a standoff, permitting application of a layer of an appropriate adherent between the gone surface and distal side 55. Such adherents are well known in the art and include poly(methylmethacrylate) bone cements, for example.

Figure 5:
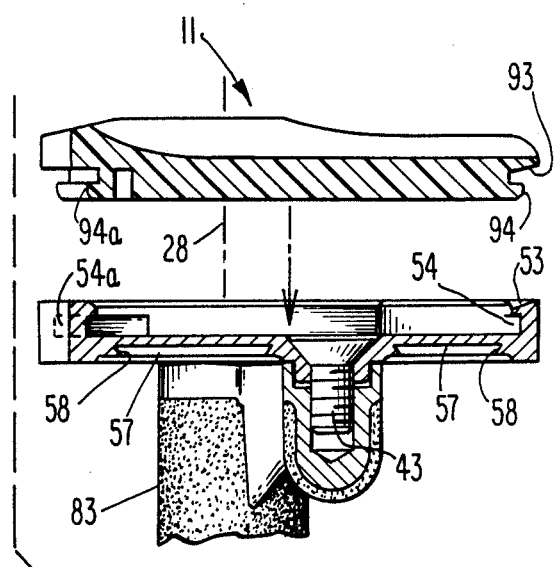
FIG. 5 is a cross-sectional view taken along section line 5—5 in FIG. 3 and includes, in addition, an exploded bearing insert in similar cross-section.
Figure 3:
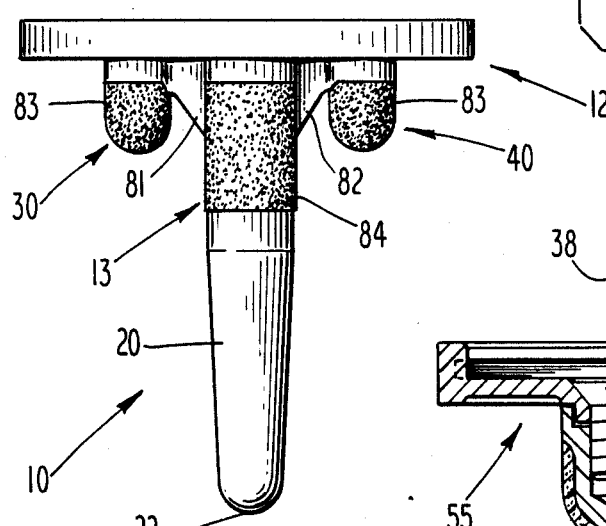
FIG. 3 is a front elevation of the embodiment shown in FIG. 2.
Figure 6:
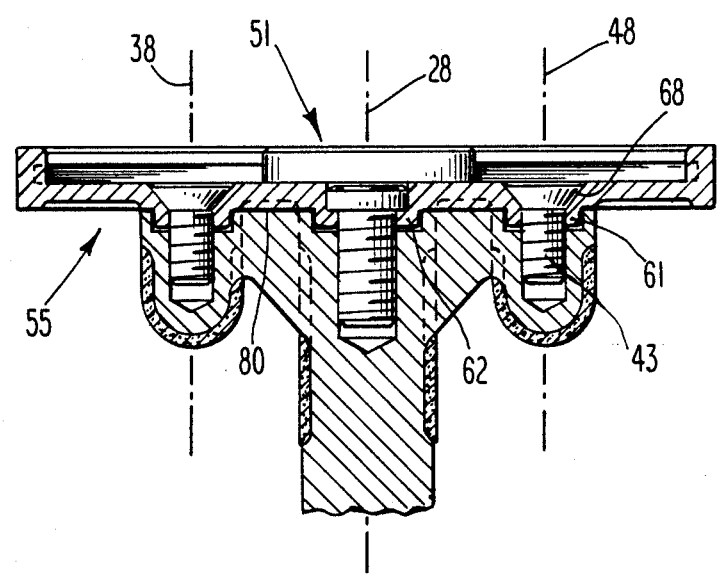
FIG. 6 is a cross-sectional view taken along section line 6—6 in FIG. 3.
Figure 4:
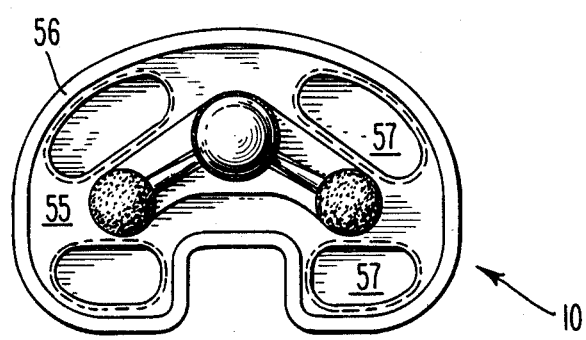
FIG. 4 is a bottom view of the embodiment shown in FIG. 2.

It is also preferred that distal side 55 include one or more walled recesses 57. When so included, it is especially preferred that recess walls 58 be angled acutely as shown in FIG. 5, thereby providing interlocking fixation of tray 12 to the tibia, e.g., via bone cement. In this way, preferred embodiments of anchorage assembly 13 exhibit "hybrid fixation" to the tibia. Immediate fixation is achieved via an adherent applied beneath tibial tray 12 and permanent fixation through longer term bone ingrowth. The immediate fixation feature encourages permanent fixation of the prosthesis via bone ingrowth by minimizing relative motion between the prosthesis and adjacent bone surfaces.

In preferred embodiments of modular tibial component 10, distal side 55 of tibial tray 12 carries one or more bosses, e.g., bosses 61 and 62, through which fasteners, e.g., screw 43, pass. Proximal termini 21, 31 and 41 are then counterbored, as shown especially in FIGS. 5 and 6, to receive the bosses, thereby interdigitating tray 12 with anchorage assembly 13 and minimizing relative motion between the two parts.

Tibial tray 12 is also adapted to removably attach to the anchorage assembly, e.g., by providing holes, e.g., hole 67, through the tray for passing fasteners 23, 33 and 43 into termini 21, 31 and 41, respectively. In order to avoid constraints on the bearing inserts the tibial tray can accommodate, the holes preferably will be counterbored or countersunk, e.g., countersink 68, on the proximal side 51 of the tibial tray opposite the bosses. In this regard, and with reference to FIGS. 5 and 6, the holes provided for fasteners 33 and 43 preferably are countersunk, rather than counterbored, to avoid structural weakness.

Tibial tray 12 viz., proximal side 51 is adapted to receive and retain a bearing insert, such as insert 11, for example. There are a number of ways in which such adaptation can be effected, depending upon the characteristics of the bearing insert. FIGS. 1-6 illustrate one way in which the proximal side can be adapted: other ways are shown in FIGS. 7 and 8.

Proximal side 51 carries axially-raised flange 52 about its periphery, and the flange is contoured at 53 to mate with corresponding contour 93 in bearing insert 11 and is provided with undercuts 54 and 54a to accept tongues 94 and 94a, respectively, of the bearing insert. Bearing insert 11 is then received and retained by these snap-fit means; other variations of such means will be apparent.

Figure 7:
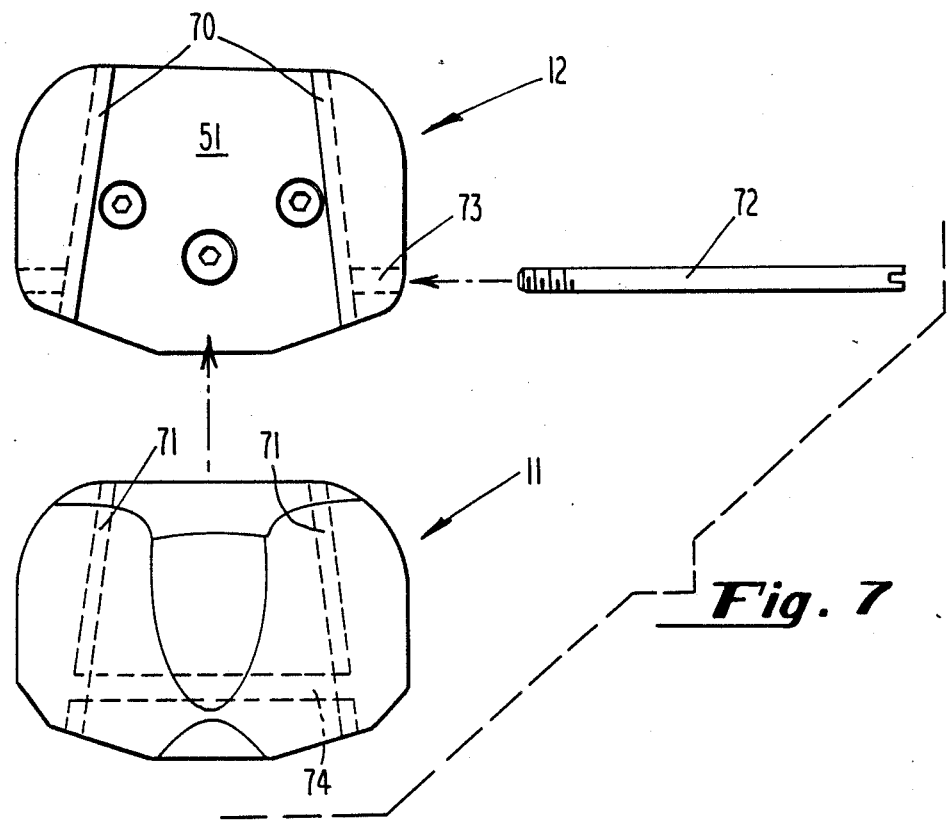
FIG. 7 is a top view showing a portion of another embodiment of this invention.

FIG. 7 illustrates an alternative adaptation of proximal side 51 of tibial tray 12 to receive and retain a modified bearing insert 11. That is, grooves 70 accept tongues 71 of the bearing insert, and the latter is locked in place by slipping pin 72 through passage 73 and mating hole 74.

Figure 8:
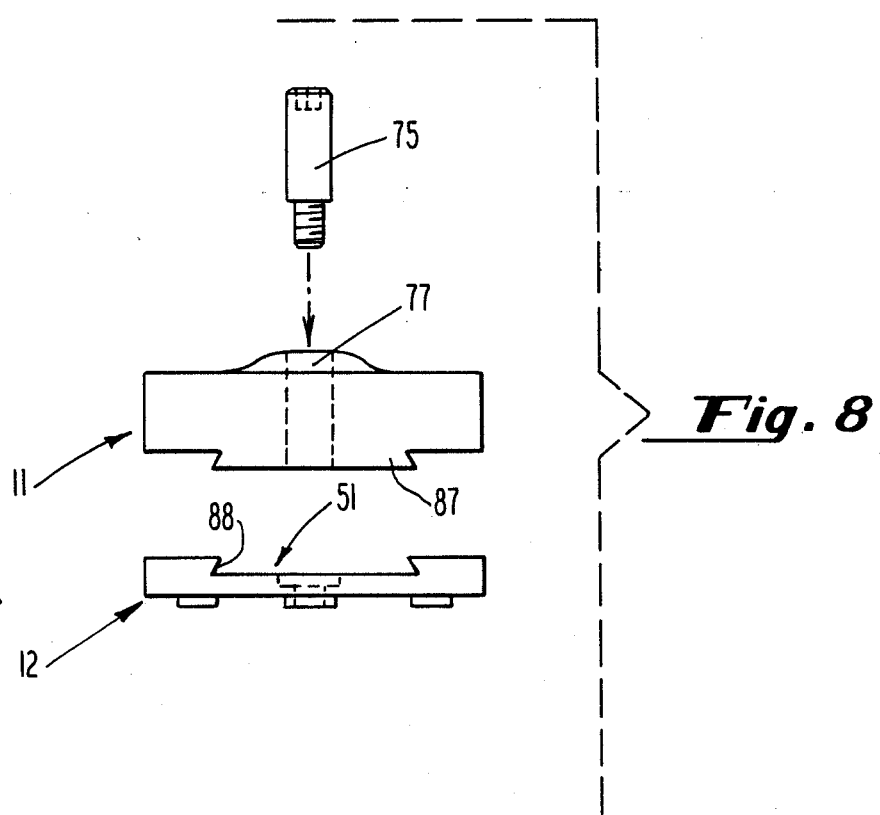
FIG. 8 is a front elevation showing a portion of still another embodiment of this invention.

In the embodiment shown in FIG. 8, mortise 88 is provided on proximal side 51 of tibial tray 12 to receive tenon 87 of bearing insert 11, and the bearing insert is adapted by providing hole 77 to receive screw 75 (a modification of fastener 23).

Figure 9:
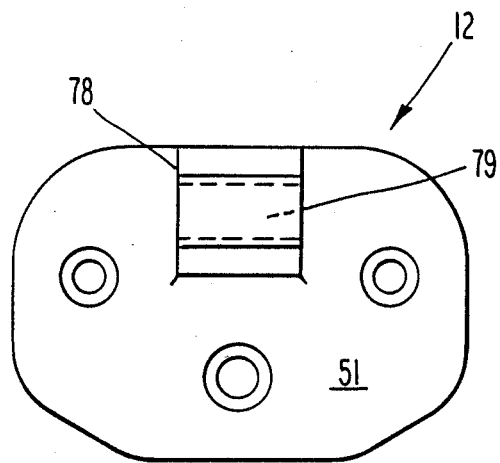
FIG. 9 is a plan view of an additional embodiment of this invention.
Figure 10:
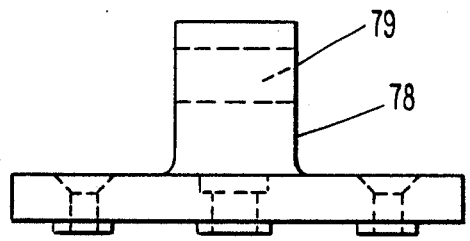
FIG. 10 is a front elevation of the embodiment shown in FIG. 9.
Figure 11:
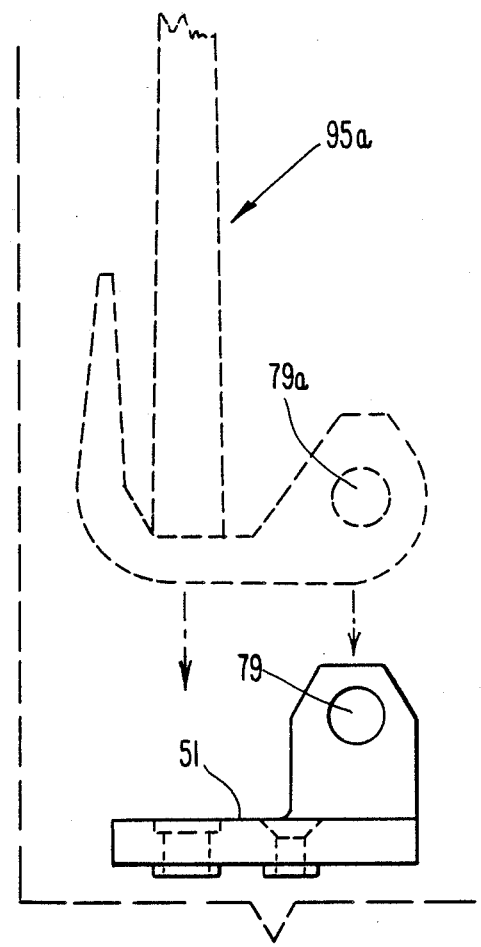
FIG. 11 is a side view of the embodiment of FIG. 9 and includes, in addition, an exploded femoral component with which the invention is used.

The embodiment of the invention illustrated in FIGS. 9–11 differs from the embodiments of FIGS. 1–8 in that the tibial tray 12 is adapted to directly receive and retain femoral component 95a without an intermediate bearing insert. That is, the embodiments of FIGS. 1–8 represent unconstrained prostheses, while the embodiment of FIGS. 9–11 is for a constrained, or "articulated", prosthesis. In the latter embodiment, proximal side 51 of tibial tray 12 is adapted by providing an integral standard 78 with passage 79 over which femoral component 95a fits to be retained by a pin (not shown) which passes through passage 79 and holes 79a in the femoral component on either side thereof.

The surgical preparation of the proximal end of the tibia and implantation of the in-bone anchorage assembly, related modular tibial component, and related tibial prosthesis of this invention in the course of restoring an injured knee is carried out using techniques which are well known in the art, the proximal tibia being prepared to receive the in-bone anchorage assembly. The following Examples present the results of laboratory tests carried out with this invention.

EXAMPLE 1

CEMENT RETENTION OF THE MODULAR TIBIAL COMPONENT

Four modular tibial components similar to the device labeled 10 in FIGS. 1–6, 76 mm wide, were press-fitted into, and tibial tray 12 was cemented onto, simulated bone (cast polyurethane) using bone cement. The cement was applied only to the distal side of the tray, not to the stem or pegs. The cement was allowed to cure for 24 hrs. For comparison, four "P.F.C." tibial components ("P.F.C." is a registered trademark of Johnson & Johnson, New Brunswick, N.J.), 71 mm wide, with keels, were similarly press-fitted into and cemented to the same simulated bone material, except that the cement was applied to both the keel and tray.

Mechanical testing was undertaken in which the force, applied at a right angle to the tray, necessary to separate the tray from the simulated bone was measured. Tests were conducted both before the cement was applied (to determine the effect of the press-fit alone) and after the cement was cured. The following results were obtained, the effect of the pressfit being subtracted:

| Device | Avg. Force (Kg) |
| --- | --- |
| "P.F.C." | 184 ± 19 |
| This Invention | 251 ± 33 |

EXAMPLE 2

FATIGUE RESISTANCE OF THE TIBIAL PROSTHESIS

Three tibial prostheses similar to that of FIGS. 1–6 were assembled with a ¼-28 Spiralock screw torqued to 6 ft-lbs in the stem and #10-32 Spiralock screws torqued to 4 ft-lbs in the pegs. The prosthesis was supported only by the central stem and one-half of the tray. The remaining one-half of the tray was left unsupported. A cyclic (8 HZ) load was applied asymmetrically to the tibial component through a mating femoral component such that 80% of a 470 Kg (6×body weight) force was applied to the unsupported side and 20% to the supported side.

Each of the three prostheses survived 10,000,000 cycles without failure or signs of tray cracking.

Although the invention has been described in detail with respect to a single preferred embodiment, it will be recognized the invention is of broader scope than that embodiment and is readily adaptable to any femoral component through modification of the tibial tray or bearing inserts. Consequently, the invention is to be accorded the scope represented in the following claims:

What is claimed is:

1. An in-bone anchorage assembly for a tibial prosthesis which comprises
   an axially elongated central stem;
   a plurality of elongated fixation pegs spaced from said stem, said stem and said pegs having proximal and distal termini, wherein the proximal termini of said stem and said pegs define an attachment table;
   a plurality of structural links interconnecting said pegs to said stem; together with
   means for removably attaching a tibial tray to said assembly, wherein each of said pegs is connected to said stem by the structural link.

2. The assembly of claim 1 wherein said stem and said pegs are disposed substantially parallel along the axes of elongation.

3. The assembly of claim 1 wherein the axes of said stem and said attachment table are substantially perpendicular.

4. The assembly of claim 1 wherein said stem and said pegs are substantially cylindrical and sized to fit within the available tibial bone stock.

5. The assembly of claim 4 wherein said stem is tapered toward said distal terminus.

6. The assembly of claim 1 wherein at least a portion of the outer surface of said assembly comprises means to enhance fixation.

7. The assembly of claim 6 wherein said fixation enhancement means comprises a porous coating.

8. The assembly of claim 7 wherein at least part of said porous coating is protuberant.

9. The assembly of claim 1 wherein at least part of the proximal one-half of the outer surface of said stem comprises means to enhance fixation.

10. The assembly of claim 1 wherein said structural links comprise fins elongated distally and terminating proximally in said attachment table.

11. The assembly of claim 1 wherein said proximal termini are adapted to receive fasteners for removably attaching said tibial tray to said assembly.

12. An in-bone anchorage assembly for a tibial prosthesis which comprises:
    a substantially cylindrical axially elongated central metal stem having proximal and distal termini and tapered toward said distal terminus, said stem carrying a protuberant porous coating on at least a portion of a proximal surface, the proximal terminus of said stem being drilled and tapped to receive a threaded fastener;
    a pair of substantially identical and cylindrical elongated metal fixation pegs having proximal and distal termini, said pegs substantially paralleling said stem axially and sized to fit within the tibial bone, said pegs being spaced from said stem to enter the posterior-lateral and posterior-medial quadrants of the tibia, respectively, the proximal termini of said stem and said pegs in triangular relationship defining an attachment table which is substantially perpendicular to the axis of said stem, said pegs having porous-coated surfaces, the proximal termini of said pegs being drilled and tapped to receive threaded fasteners, together with a pair of narrow metal fins elongated distally from said attachment table and interconnecting said pegs with said stem, said fins having a cross-section tapering distally;

whereby a tibial tray can be removably attached to the assembly using threaded fasteners received in the proximal termini of said central stem and pegs, permitting bone-sparing access to the anchorage assembly for repair or revision.

13. A modular tibial component which comprises a bone anchorage assembly which includes an axially elongated central stem having proximal and distal termini; a plurality of elongated fixation pegs having proximal and distal termini and spaced from said stem, the proximal termini of said stem and said pegs defining an attachment table; a plurality of structural links interconnecting said pegs to said stem; together with means for removably attaching a tibial tray to said assembly, wherein each of said pegs is connected to said stem by said structural link; a flattened tibial tray having a proximal surface and a distal surface, said tray being adapted to mate with a prepared tibia, and the modular tibial component being adapted to receive and retain a bearing element on the proximal surface of said tray.

14. The tibial component of claim 13 wherein the distal surface of said tray carries a narrow flange extending distally about its periphery.

15. The tibial component of claim 13 wherein the distal surface of said tray includes at least one walled recess, said wall being angled with respect to said distal surface to provide interlocking fixation to the tibia.

16. The tibial component of claim 13 wherein the proximal termini of said stem and said pegs are drilled and tapped to receive threaded fasteners in corresponding holes drilled through said tray, and said termini are counterbored to receive corresponding raised bosses which are provided on the distal side of said tray, thereby permitting said tibial tray to interdigitate with and removably attach to said anchorage assembly.

17. The tibial component of claim 16 wherein said holes are counterbored/countersunk in said tibial tray opposite said bosses.

18. The tibial component of claim 13 wherein the proximal surface of said tray carries an axially raised flange about its periphery, and said flange is contoured to mate with complementary structure in said bearing element.

19. A modular tibial component to mate with a bearing insert which comprises an in-bone anchorage assembly including a substantially cylindrical axially elongated central metal stem having proximal and distal termini and tapered toward said distal terminus, said stem carrying a protuberant porous coating on at least a portion of a proximal surface, the proximal terminus of said stem being drilled and tapped to receive a threaded fastener;

a pair of substantially identical and cylindrical metal fixation pegs having proximal and distal termini, said pegs being aligned substantially parallel to said stem axially and sized to fit within the available tibial bone stock, said pegs being spaced from said stem to enter the posterior-lateral and posterior-medial quadrants of the tibia, respectively, the proximal termini of said stem and said pegs in triangular relationship defining an attachment table which is substantially perpendicular to the axis of said stem, said pegs having porous-coated surfaces, the proximal termini of said pegs being drilled and tapped to receive threaded fasteners; together with a pair of narrow metal fins elongated distally from said attachment table and interconnecting said pegs with said stem, said fins having a cross-section tapering distally; in combination with a flattened metal tibial tray having a proximal surface and a distal surface;

said tray being removably attachable to said attachment table of the in-bone anchorage assembly by means of threaded fasteners through holes drilled through said tibial tray, said holes being counterbored/countersunk on the proximal surface of said tray, with raised bosses coaxial with said holes provided on the distal surface of said tray to interdigitate with complementary counterbores provided in the drilled and tapped proximal termini of said stem and said pegs;

the distal surface of said tray including a narrow axially-raised flange extending distally about its periphery and at least one walled recess in said distal surface, said wall being angled with respect to aid distal surface to provide interlocking fixation to the tibia; together with an axially-raised flange on the proximal surface of said tray about its periphery, said flange being contoured to mate with complementary structure in a bearing element;

whereby the bearing element can be removed or replaced, and the tibial tray can be removed, permitting bone-sparing access to the in-bone anchorage assembly for repair or revision.

20. A tibial prosthesis comprising a modular tibial component which includes in combination a bearing element; an in-bone anchorage assembly comprising an axially elongated central stem having proximal and distal termini; a pluality of elongated fixation pegs having proximal and distal termini and spaced from said stem, the proximal termini of said stem and said pegs defining an attachment table; a plurality of structural links interconnecting said pegs to said stem; together with means for removably attaching a tibial tray to said assembly, wherein each of said pegs is connected to the stem by said structural link; and a flattened tibial tray having a proximal surface and a distal surface, said tray being adapted to removably attach to said attachment table of the in-bone anchorage assembly, the distal surface of said tray being adapted to mate with a prepared tibia, and the modular tibial component being adapted to receive and retain said bearing element on the proximal surface of said tray.

21. The method of restoring an injured knee which comprises surgically preparing the proximal end of the tibia and implanting therein an in-bone anchorage assembly comprising an axially-elongated central stem having proximal and distal termini;

a plurality of elongated fixation pegs having proximal and distal termini and spaced from said stem, the proximal termini of said stem and said pegs defining an attachment table;

a plurality of structural links interconnecting said pegs to said stem; together with means for removably attaching a tibial tray to said assembly, wherein each of said pegs is connected to the stem by said structural link.

22. The method of restoring an injured knee which comprises surgically preparing the proximal end of the tibia and implanting therein a modular tibial component which includes in combination an in-bone anchorage assembly comprising an axially-elongated central stem having proximal and distal termini;

a plurality of elongated fixation pegs having proximal and distal termini and spaced from said stem, the proximal termini of said stem and said pegs defining an attachment table;

a plurality of structural links interconnecting said pegs to said stem; together with means for removably attaching a tibial tray to said assembly, wherein each of said pegs is attached to said stem by said structural link; and a flattened tibial tray having a proximal surface and a distal surface, said tray being adapted to removably attach to said attachment table of the in-bone anchorage assembly, the distal surface of said tray being adapted to mate with a prepared tibia, and the modular tibial component being adapted to receive and retain a bearing element on the proximal surface of said tray.

* * * * *